(12) United States Patent
Suzuki et al.

(10) Patent No.: US 10,238,616 B2
(45) Date of Patent: Mar. 26, 2019

(54) IMMUNOMODULATOR

(71) Applicant: WAKUNAGA PHARMACEUTICAL CO., LTD., Osaka-shi (JP)

(72) Inventors: Junichiro Suzuki, Hiroshima (JP); Yukihiro Kodera, Hiroshima (JP); Kenji Itoh, Miyoshi (JP); Toshiaki Matsutomo, Aki-gun (JP)

(73) Assignee: WAKUNAGA PHARMACEUTICAL CO., LTD., Osaka-shi (JP)

(*) Notice: Subject to any disclaimer, the term of this patent is extended or adjusted under 35 U.S.C. 154(b) by 0 days.

(21) Appl. No.: 15/532,745

(22) PCT Filed: Dec. 4, 2015

(86) PCT No.: PCT/JP2015/084201
§ 371 (c)(1),
(2) Date: Jun. 2, 2017

(87) PCT Pub. No.: WO2016/088892
PCT Pub. Date: Jun. 9, 2016

(65) Prior Publication Data
US 2017/0360731 A1     Dec. 21, 2017

(30) Foreign Application Priority Data

Dec. 5, 2014 (JP) ................. 2014-246973

(51) Int. Cl.
*A61K 31/198* (2006.01)
*A61K 36/8962* (2006.01)

(52) U.S. Cl.
CPC ........ *A61K 31/198* (2013.01); *A61K 36/8962* (2013.01)

(58) Field of Classification Search
CPC .......................... A61K 31/198; A61K 36/8962
See application file for complete search history.

(56) References Cited

U.S. PATENT DOCUMENTS

| 6,239,111 | B1 | 5/2001 | Moriguchi et al. | |
| 6,340,483 | B1 * | 1/2002 | Goren | A61K 36/8962 424/754 |

FOREIGN PATENT DOCUMENTS

| JP | 4-338336 | 11/1992 |
| JP | 5-60447 B2 | 9/1993 |
| JP | 2008-31122 | 2/2008 |
| JP | 4255138 B2 | 4/2009 |
| JP | 2014-1170 | 1/2014 |
| JP | 2014-23449 | 2/2014 |
| WO | WO 2011/053815 A1 | 5/2011 |
| WO | WO 2011/118067 A | 9/2011 |

OTHER PUBLICATIONS

Lucia M Kato, et al., Immunology and Cell Biology, 2014, vol. 92(1): pp. 49 to 50.
Sidonia Fagarasan, et al., "Intestinal IgA Synthesis: Regulation of Front-Line Body Defences", Nature Reviews, Immunology, Jan. 2003, vol: 3(1): pp. 63 to 72.
AJ Macpherson, et al., The immune geography of IgA induction and function, Mucosal Immunology, Jan. 2008, vol. 1, No. 1, pp. 11 to 22.
Karmtej Singh, et al., "IgA deficiency and Autoimmunity", Autoimmunity Reviews, 2014, 13(2), pp. 163 to 177.
Tadamitsu Kishimoto, et al., "Interleukin-6 and its Receptor: A Paradigm for Cytokines", Science, Oct. 1992, vol. 258: pp. 593 to 597.
Toshio Tanaka, et al., "IL-6 in Inflammation, Immunity, and Disease", Cold Spring Harbor Perspectives in Biology, 2014, 6(10): pp. 1 to 16.
Ninniku no Kagaku (Garlic Science), first edition, supervised by Hiroshi Saito, Asakura Publishing Co., Ltd., 2000, pp. 93 to 122 (with partial English translation).
Shizutoshi Nakagawa, et al., "prevention of Liver Damage by Aged Garlic Extract and its Components in Mice", Phylotherapy Research, 1989, vol. 3, No. 2, pp. 50 to 53.
Shunso Hatono, et al., "Chemopreventive effect of S-allylcysteine and its relationship to the detoxification enzyme glutathione S-transferase", Carcinogenesis, 1996, vol. 17, No. 5, pp. 1041 to 1044.
J.F. Carson, et al., The Synthesis and Base Catalyzed Cyclization of (+)and (−)-cis-S-(1-propenyl)-L-cysteine Sulfoxides, The Journal of Organic Chemistry, 1966, vol. 31, No. 9, pp. 2862-2864.
Extended European Search Report issued May 14, 2018 in European Patent Application No. 15864982.2, citing documents AO, and AX through AZ therein, 8 pages.
Corzo-Martinez, M. et al., "Biological Properties of Onions and Garlic", Trends in Food Science & Technology, vol. 18, No. 12, XP55290781, Dec. 1, 2007, pp. 609-625.
Imai, J., et al., "Antioxidant and Radical Scavenging Effects of Aged Garlic Extract and its Constituents", Planta Medica, vol. 60, No. 5, XP009505098,1994, pp. 417-420.
Lee, S., et al., "Facile Synthesis of trans-S-1-Propenyl-L-Cysteine Sulfoxide (Isoalliin) in onions (*Allium cepa*)", Bull Korean Chem. Soc., vol. 32 No. 1, XP002780689, 2011, pp. 319-320.

* cited by examiner

*Primary Examiner* — Zohreh A Fay
(74) *Attorney, Agent, or Firm* — Oblon, McClelland, Maier & Neustadt, L.L.P.

(57)   ABSTRACT

An immunomodulator useful for modulating immune function and maintaining intravital homeostasis is provided. The immunomodulator comprises S-1-propenycysteine or a salt thereof as an active ingredient.

7 Claims, 9 Drawing Sheets

[Figure 7]
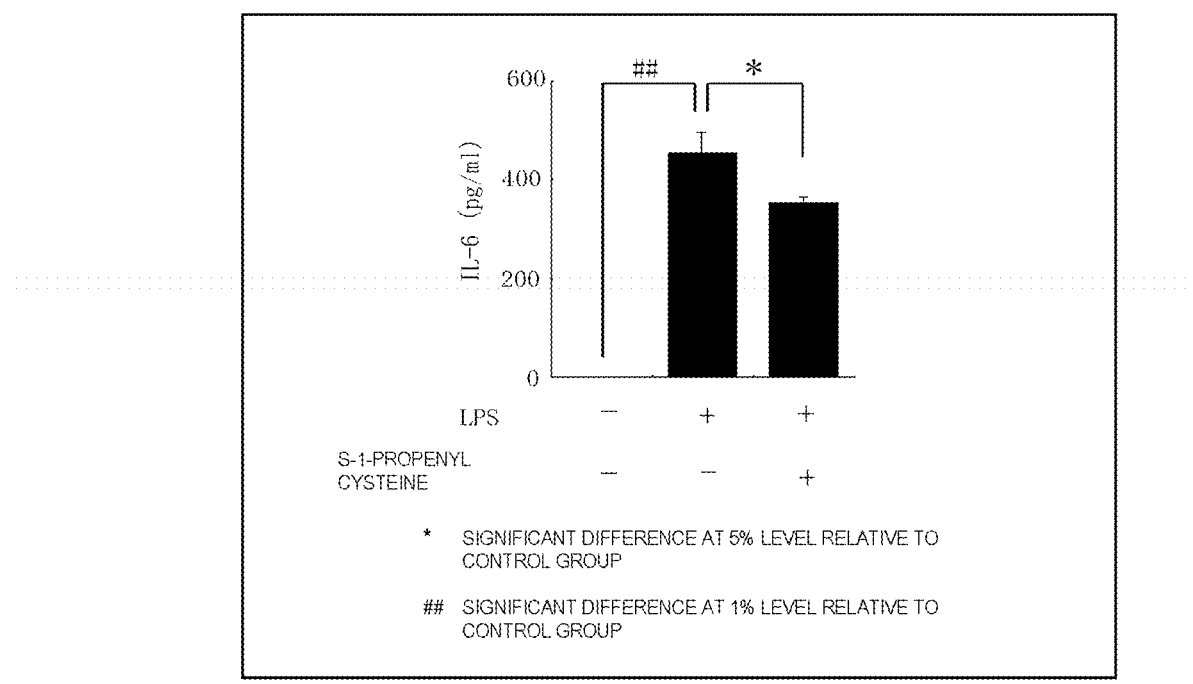

[Figure 8]
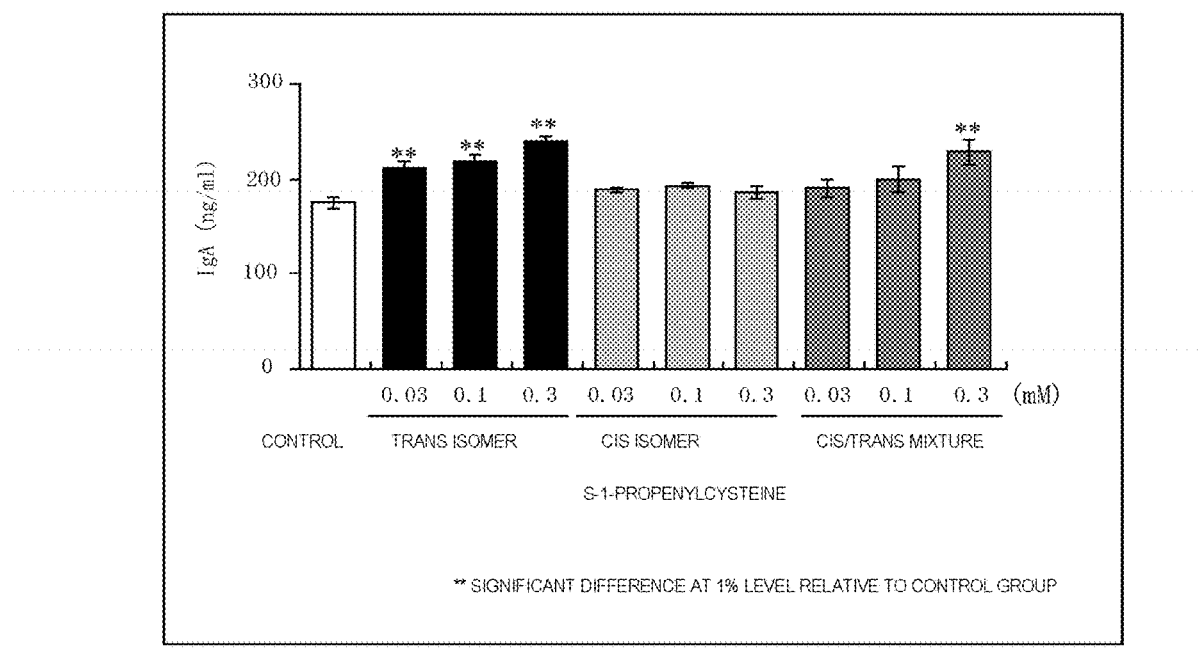

[Figure 9]
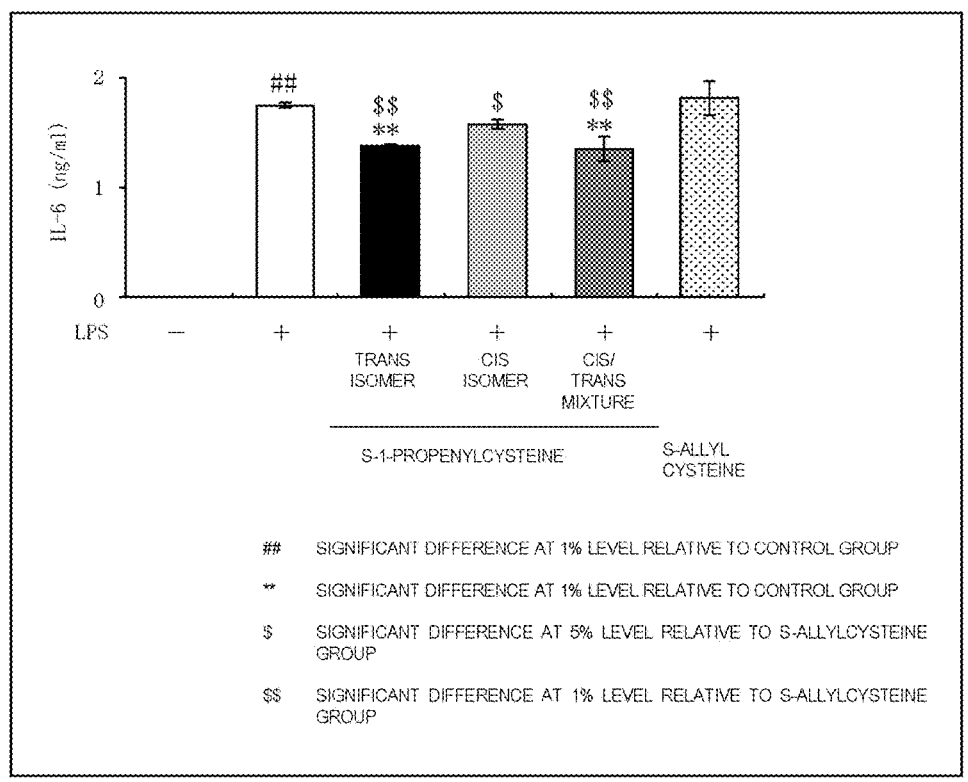

IMMUNOMODULATOR

TECHNICAL FIELD

The present invention relates to an immunomodulator useful for maintaining intravital homeostasis.

BACKGROUND ART

Immunoglobulin A (IgA) is an antibody secreted most abundantly in mammals. It is secreted by IgA-producing cells in the lamina propria in the intestinal tract. IgA mainly functions to maintain homeostasis in the body through protecting the body from foreign pathogens contained in food or invading pathogenic bacteria and through maintaining the balance of intestinal bacterial flora (Non Patent Literatures 1 to 3). It is known that patients with IgA deficiency have a higher incidence of allergic disease and autoimmune disease (Non Patent Literature 4).

Interleukin-6 (IL-6), one of the cytokines produced by T cells and macrophages, plays a role in promoting hematopoiesis and differentiation into antibody-producing cells. On the other hand, when overproduced, it also acts to enhance inflammatory responses by, for example, causing chronic inflammation or autoimmune disease (Non Patent Literatures 5 and 6).

In view of the above, an attempt to modulate immune function by promoting IgA production and inhibiting the overproduction of IL-6 is useful for maintaining homeostasis in the body, preventing the development of allergy, and inhibiting inflammatory responses.

Meanwhile, γ-glutamyl-S-allylcysteine is a characteristic component of garlic. When garlic is cut, crushed, grated, or aged, this component is converted to water-soluble S-allylcysteine (here in below, abbreviated as SAC) by γ-glutamyltranspeptidase, an enzyme contained in garlic. In addition to SAC, there are other water-soluble compounds produced by such an enzymatic reaction, which are, for example, S-methylcysteine and S-1-propenylcysteine (Non Patent Literature 7).

There are numerous reports about the pharmacological action of SAC such as hepatoprotective effects (Non Patent Literature 8 and Patent Literature 1) and anti-colon cancer effects (Non Patent Literature 9). Further, S-methylcysteine has also been reported to have hepatoprotective effects (Patent Literature 2), cerebropathy improving effects (Patent Literature 1), and so on.

However, there has been no report about the pharmacological action of S-1-propenylcysteine, and it is totally unknown that S-1-propenylcysteine has immunomodulatory effects such as promoting effect of IgA production and inhibitory effect of IL-6 production.

CITATION LIST

Patent Literature

[Patent Literature 1] JP-B-4255138
[Patent Literature 2] JP-B-05-060447

Non Patent Literature

[Non Patent Literature 1] L M Kato, S Kawamoto, M Maruya, S Fagarasan. Gut TFH and IgA: key players for regulation of bacterial communities and immune homeostasis. Immunol Cell Biol. 2014; 92(1): pp. 49 to 56.
[Non Patent Literature 2] S Fagarasan, T Honjo. Intestinal IgA synthesis: regulation of front-line body defenses. Nat Rev Immunol. 2003; 3(1): pp. 63 to 72.
[Non Patent Literature 3] A J Macpherson, K D McCoy, F E Johansen, P Brandtzaeg. The immune geography of IgA induction and function. Mucosal Immunol. 2008; 1(1): pp. 11 to 22.
[Non Patent Literature 4] K Singh, C Chang, M E Gershwin. Autoimmun Rev.: IgA deficiency and autoimmunity. 2014; 13(2): pp. 163 to 177.
[Non Patent Literature 5] T Kishimoto, S Akira, T Taga. Interleukin-6 and its receptor: A paradigm for cytokines. Science, 1992; 258: pp. 593 to 597.
[Non Patent Literature 6] T Tanaka, M Narazaki, T Kishimoto. IL-6 in Inflammation, Immunity, and Disease. Cold Spring Harb Perspect Biol. 2014; 6(10): pp. 1 to 16.
[Non Patent Literature 7] *Ninniku no Kagoku* (Garlic Science), first edition, supervised by Hiroshi Saito, Asakura Publishing Co., Ltd., pp. 93 to 122, 2000.
[Non Patent Literature 8] S Nakagawa, S Kasuga, H Matsuura, Prevention of liver damage by aged garlic extract and its components in mice. Phytother. Res. 1989; 3, pp. 50 to 53.
[Non Patent Literature 9] S Hatono, A Jimenez, M J Wargovich, Chemopreventive effect of S-allylcysteine and its relationship to the detoxification enzyme glutathione 5-transferase. Carcinogenesis. 1996; 17(5): pp. 1041 to 1044.

SUMMARY OF INVENTION

Technical Problem

The present invention relates to a provision of an immunomodulator useful for modulating immune function and maintaining intravital homeostasis.

Solution to Problem

The present inventors examined the usefulness of plants containing sulfur-containing amino acid compounds and their components from various aspects. As a result, they have found that S-1-propenylcysteine or a salt thereof has excellent promoting effect of IgA production and inhibitory effect of IL-6 production, and is useful as an immunomodulator, thereby completing the present invention.

That is, the present invention relates to the following 1) to 12).
1) An immunomodulator comprising S-1-propenylcysteine or a salt thereof as an active ingredient.
2) The immunomodulator according to the above 1), wherein the S-1-propenylcysteine has the proportion of trans isomer of from 50 to 100% when the sum total of trans and cis isomers is 100%.
3) The immunomodulator according to the above 1) or 2), wherein immunomodulatation is based on promoting effect of IgA production and/or inhibitory effect of IL-6 production.
4) The immunomodulator according to any of the above 1) to 3), wherein the S-1-propenylcysteine or a salt thereof is derived from one or more plants belonging to the genus *Allium* selected from the group consisting of garlic, onion, elephant garlic, Chinese chive, and Welsh onion.
5) The immunomodulator according to the above 4), wherein the S-1-propenylcysteine or a salt thereof is obtained by extracting the plant belonging to the genus *Allium* in a 10 to 50% aqueous solution of ethanol at 0 to 80° C. for one month or more, allowing the extract thus obtained to adsorb to a cation exchange resin, carrying out elution using 0.1 to 3 N ammonia water, and then subjecting the eluate thus obtained to silica gel column chromatography and/or reversed-phase column chromatography to collect S-1-propenylcysteine or a salt thereof.

6) The immunomodulator according to any of the above 1) to 5), which is medicine.

7) The immunomodulator according to any of the above 1) to 5), which is food.

8) A method for producing S-1-propenylcysteine or a salt thereof, comprising extracting a plant belonging to the genus *Allium* in a 10 to 50% aqueous solution of ethanol at 0 to 80° C. for one month or more, allowing the extract thus obtained to adsorb to a cation exchange resin, carrying out elution using 0.1 to 3 N ammonia water, and then subjecting the eluate thus obtained to silica gel column chromatography and/or reversed-phase column chromatography to collect S-1-propenylcysteine or a salt thereof.

9) The production method according to the above 8), wherein the plant belonging to the genus *Allium* is one or more selected from the group consisting of garlic, onion, elephant garlic, Chinese chive, and Welsh onion.

10) Use of S-1-propenylcysteine or a salt thereof for the production of an immunomodulator.

11) S-1-propenylcysteine or a salt thereof for use in immunomodulation.

12) A method for immunomodulation, comprising administering S-1-propenylcysteine or a salt thereof.

Advantageous Effects of Invention

The immunomodulator of the present invention can mitigate the invasion of external foreign substances or the damage caused by the invasion, and maintain intravital homeostasis through its immunomodulatory effects such as promoting IgA production and inhibiting IL-6 production. Further, the immunomodulator of the present invention can inhibit inflammatory and allergic responses.

BRIEF DESCRIPTION OF DRAWINGS

FIG. 7 is a graph illustrating inhibitory effect of S-1-propenylcysteine on IL-6 production under LPS stimulation.

FIG. 8 is a graph illustrating promoting effect of S-1-propenylcysteine (cis isomer, trans isomer, and cis/trans mixture) on IgA production.

FIG. 9 is a graph illustrating inhibitory effects of S-1-propenylcysteine (cis isomer, trans isomer, and cis/trans mixture) and SAC on IL-6 production under LPS stimulation.

DESCRIPTION OF EMBODIMENTS

Figure 1:
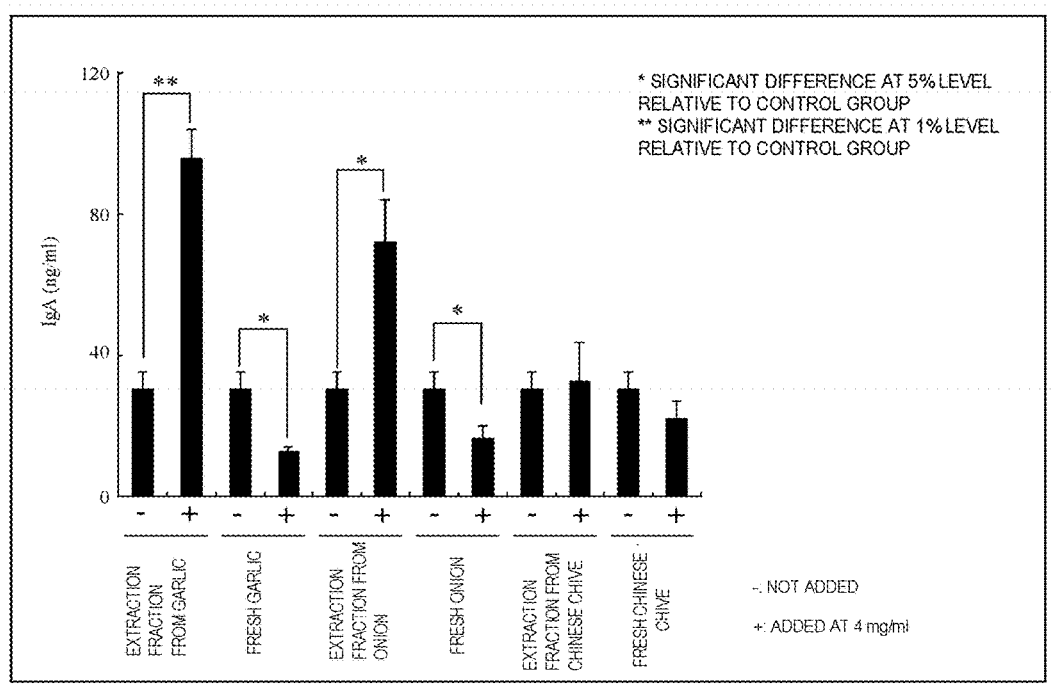
FIG. 1 is a graph illustrating promoting effect of fractions obtained by extraction of plants belonging to the genus *Allium* with aqueous solutions of ethanol on IgA production.

In the present invention, S-1-propenylcysteine is a cysteine derivative represented by formula (1) shown below.

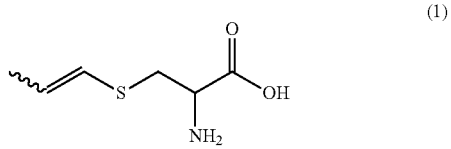

(1)

As indicated by a wavy line, this compound exists in cis or trans conformation, and S-1-propenylcysteine with a higher proportion of trans isomer is preferable. When the sum total of trans and cis isomers is 100%, the proportion of trans isomer is more preferably from 50 to 100%, even more preferably from 75 to 100%, further more preferably from 80 to 100%, further more preferably from 90 to 100%.

In addition, S-1-propenylcysteine can include optical isomers due to an asymmetric carbon in the cysteine moiety; however, this compound may be in any of D-, L-, and racemic mixtures.

A salt of S-1-propenylcysteine may be an acid addition salt or a base addition salt. Examples of the acid addition salt include (i) a salt with a mineral acid such as hydrochloric acid, sulfuric acid, nitric acid, or phosphoric acid, (ii) a salt with an organic carboxylic acid such as formic acid, acetic acid, citric acid, fumaric acid, gluconic acid, malic acid, succinic acid, tartaric acid, trichloroacetic acid, or trifluoroacetic acid, and (iii) a salt with a sulfonic acid such as methanesulfonic acid, benzenesulfonic acid, p-toluenesulfonic acid, mesitylenesulfonic acid, or naphthalenesulfonic acid. Also, examples of the base addition salt include (i) a salt with an alkali metal such as sodium or potassium, (ii) a salt with an alkaline earth metal such as calcium or magnesium, (iii) an ammonium salt, and (iv) a salt with a nitrogen-containing organic base such as trimethylamine, triethylamine, tributylamine, pyridine, N,N-dimethylaniline, N-methylpiperidine, N-methylmorpholine, dietbylamine, dicyclohexylamine, procaine, dibenzylamine, N-benzyl-β-phenethylamine, 1-ephenamine, or N,N'-dibenzylethylenediamine.

Further, S-1-propenylcysteine or a salt thereof can exist not only in unsolvated form, but also as a hydrate or solvate. Such hydrates or solvates can exist as any form of crystal depending on the production conditions. Accordingly, the S-1-propenylcysteine or a salt thereof of the present invention encompasses all stereoisomers, hydrates, and solvates as well as all crystal polymorphs or amorphous forms.

The S-1-propenylcysteine or a salt thereof of the present invention can be obtained by an organic synthesis technique [1] H Nishimura, A Mizuguchi, J Mizutani, Stereoselective synthesis of S-(trans-prop-1-enyl)-cysteine sulphoxide Tetrahedron Letter, 1975, 37, pp. 3201 to 3202; 2] J C Namyslo, C Stanitzek, A palladium-catalyzed synthesis of isoalliin, the main cysteine sulfoxide in Onion (*Allium cepa*). Synthesis, 2006, 20, pp. 3367 to 3369; 3] S Lee, J N Kim, D H Choung, H K Lee, Facile synthesis of trans-S-1-propenyl-L-cysteine sulfoxide (isoalliin) in onions (*Allium cepa*). Bull. Korean Chem. Soc. 2011, 32(1), pp. 319 to 320], a biochemical technique using enzymes or microorganisms, or a combined method of these techniques. Moreover, the S-1-propenylcysteine or a salt thereof of the present invention can also be obtained by carrying out extraction and purification using a plant containing the above compound such as a plant belonging to the genus *Allium* or its processed product.

Accordingly, as the S-1-propenylcysteine or a salt thereof of the present invention, not only an isolated and purified product, but also a crude product and fraction in which the content of S-1-propenylcysteine or a salt thereof is increased by operations of extraction of the foregoing plant can be used.

At this point, examples of the plant belonging to the genus *Allium* containing S-1-propenylcysteine or a salt thereof include garlic (*Allium sativum* L.), onion (*Allium cepa* L.), elephant garlic (*Allium ampeloprasum* L.), Chinese chive (*Allium tuberosum*. Rottl. Ex K. Spreng.), and Welsh onion (*Allium fistulosum* L.). These plants can be used alone or in combination. The foregoing plants belonging to the genus *Allium* can be used as is (raw) or, if necessary, after peeling the outer skin, followed by cutting or shredding. Further, plants that have been dried by freeze-drying or hot air-drying, or powderized products of these dried plants can also be used.

When using an extraction fraction of a plant belonging to the genus *Allium* as the S-1-propenylcysteine or a salt thereof of the present invention, the fraction can be obtained, for example, by 1) extracting a plant belonging to the genus *Allium* in a 10 to 50% aqueous solution of ethanol at 0 to 80° C. for one month or more, 2) subjecting the extract thus obtained to solid-liquid separation, and then collecting elution fraction by using an aqueous solution of ethanol.

As the aqueous solution of ethanol used in step 1), a 10 to 50% aqueous solution of ethanol can be used; however, an aqueous solution of ethanol adjusted to an ethanol concentration of from 20 to 40% is preferably used. The treatment temperature can be set in a range of from 0 to 80° C., preferably in a range of from 10 to 60° C., more preferably in a range of from 20 to 40° C. As to the treatment period, extraction can be carried out for at least one month, preferably for from 1 to 20 months, more preferably for from 1 to 10 months under the foregoing conditions. Taking into consideration the sanitary aspects, volatility of ethanol, and so on, this step can be carried out in an airtight, sealed, or closed container. It is preferable to use a closed container.

In step 2), after subjecting the extract obtained in step 1) to solid-liquid separation, the fraction obtained by elution using an aqueous solution of ethanol is collected. Then, by concentrating the collection as appropriate, an extraction fraction containing S-1-propenylcysteine or a salt thereof can be obtained. It is also possible to dry the collection by means of, for example, spray drying as appropriate and use the resulting dried product.

Further, S-1-propenylcysteine or a salt thereof can be isolated from the foregoing extraction fraction containing S-1-propenylcysteine or a salt thereof by performing dialysis using a dialysis membrane with a molecular size cut-off range of 3,000 to 4,000, as needed, and then appropriately combining adsorption/separation using a cation exchange resin and a separation and purification means by using normal phase chromatography or reversed-phase chromatography.

At this point, the adsorption/separation using a cation exchange resin can be performed by a method involving allowing S-1-propenylcysteine or a salt thereof to adsorb to a cation exchange resin (such as AMBERLITE (the product of The Dow Chemical Company), DOWEX (the product of The Dow Chemical Company), and DIATOM (the product of Mitsubishi Chemical Corporation)), followed by elution using 0.1 to 3 N ammonia water.

For normal phase chromatography, for example, a method of using a silica gel column and performing elution using, for example, a chloroform/methanol/water mixture can be employed.

For reversed-phase chromatography, for example, a method of using an octadecylsilyl column and performing elution using, for example, a 0.01 to 3% aqueous solution of formic acid can be employed.

Preferably, the following method can be employed: A method involving dialyzing the foregoing extraction fraction of the aqueous solution of ethanol (dialysis membrane: a molecular size cut-off range of 3,000 to 4,000), allowing the product of interest to adsorb to a cation exchange resin, then eluting it with 0.5 to 2 N ammonia water, subjecting the eluate thus obtained to silica gel column chromatography (solvent: a chloroform/methanol/water mixture) to collect a fraction containing the product of interest, and further subjecting the fraction to preparative reversed-phase column chromatography (solvent: a 0.1 to 0.5% aqueous solution of formic acid) to collect the product of interest.

In the S-1-propenylcysteine thus obtained, the proportion of trans isomer is more preferably from 50 to 95%, even more preferably from 60 to 90%, further more preferably from 70 to 90%, when the sum total of trans and cis isomers is 100%.

As will be demonstrated in Examples later, S-1-propenylcysteine or a salt thereof has not only excellent IgA-producing action, but also excellent inhibitory effect of IL-6 production under LPS stimulation, as compared to other cysteine derivatives such as S-allylcysteine, S-methylcysteine, and γ-glutamyl-S-allylcysteine. Therefore, S-1-propenylcysteine or a salt thereof can serve as an immunomodulator based on its IgA production-promoting effect and/or inhibitory effect on IL-6 production IgA functions to prevent the invasion of pathogenic microorganisms and allergens and maintain intravital homeostasis, while contributing to the prevention of the development of allergy. Meanwhile, IL-6 plays a central role in the normal immune response and host defense such as induction of antibody production from B cells and activation of T lymphocytes. On the other hand, the overexpression of IL-6 has been reported to be associated with pathogenesis and exacerbation of chronic inflammation such as chronic rheumatoid arthritis and osteoarthritis, and immune disorder (Non Patent Literatures 1 to 6 shown above). In light of the above, an attempt to modulate immune function by promoting IgA production and inhibiting the overproduction of IL-6 is useful for maintaining intravital homeostasis, preventing development of allergy, and inhibiting inflammatory responses.

In the present invention, "immunomodulation" means modulation of immune function mainly based on IgA production-promoting effect and/or inhibitory effect on IL-6 production, whereby the effects such as the maintenance of intravital homeostasis, prevention of the development of allergy, and inhibition of inflammatory responses are exerted. Here, promoting IgA production includes increasing IgA-producing cells and/or increasing the amount of IgA secreted from these cells.

The immunomodulator of the present invention can be a medicine or food, which exerts immunomodulatory effects such as IgA production-promoting effect and inhibitory effect on IL-6 production per se upon ingestion by (including administration to) humans, or it can be an ingredient or preparation to be incorporated into a medicine or food.

The food encompasses foods, functional foods, patient foods, and foods for specified health uses which have a concept of providing promoting effect on IgA production, inhibitory effect on IL-6 production, and immunomodulatory effect are labeled accordingly as needed.

The foregoing medicine or food can be a solid such as powder or granule, a semi-solid product in a form of paste or oil, or a liquid. If needed, preservatives and additives may be added. Further, the foregoing medicine or food may contain other substances having immunomodulatory effects such as sugars, sugar alcohols and polysaccharides, glycoproteins such as lectin, glycolipids such as lipopolysaccharides, and useful bacteria such as *Lactobacillus, Bifidobacterium*, yeast or *Aspergillus oryzae*.

The dosage form of the medicine containing S-1-propenylcysteine or a salt thereof of the present invention is not particularly limited and may be in various dosage forms. The medicine is preferably in the dosage form suitable for oral administration. Specific examples of the dosage form of preparations for oral administration include, as a solid agent, tablet, capsule, fine granule, pill, and granule, and as a liquid agent, emulsion, solution, suspension, and syrup. These medicinal preparations can be prepared in accordance with a routine method by appropriately combining an excipient, a binder, a disintegrant, a lubricant, a colorant, a corrigent, a pH adjuster, and the like with the S-1-propenylcysteine or a salt thereof of the present invention as needed.

The food containing S-1-propenylcysteine or a salt thereof of the present invention can be in various forms without particular limitation such as solid food, semi-fluid food, gel-like food, tablet, caplet, and capsule. More specifically, the food containing S-1-propenylcysteine or a salt thereof of the present invention can be in various forms such as snack, beverage, seasoning, processed seafood product, processed meat product, bread, and health food.

These foods can be produced in accordance with a routine method by appropriately combining food ingredients normally used for the production of these foods with the S-1-propenylcysteine or a salt thereof of the present invention.

A preferable daily intake of the foregoing medicine or food varies depending on factors such as the subject who ingests the medicine or food, the ingestion form, the types of ingredient, additive, etc. which are taken together, and the interval between ingestions. It is preferable to ingest typically from 0.1 to 2.7 mg/kg daily, more preferable to ingest from 0.3 to 0.9 mg/kg daily in terms of S-1-propenylcysteine or its salts. If desired, the above daily intake can be taken in two to four divided intakes.

The subject who receives the foregoing medicine or food is not particularly limited as long as the subject is in need of the medicine or food. The subject is preferably a human who desires to prevent or improve loss of the homeostasis system or immune function.

EXAMPLES

Production Example 1 Production of Plant Extraction Fractions Containing S-1-propenylcysteine (1) Fraction Extracted from Garlic with an Aqueous Solution of Ethanol About 1 kg of peeled garlic bulbs and about 1,000 mL of 30% ethanol were placed in a container and the container was sealed. The container was then left to stand for 1 to 10 months at room temperature, with occasional stirring. The resulting mixture was separated into solid and liquid and the liquid was dried by spray drying to obtain a yellowish brown powder.

(2) Fraction Extracted from Onions with an Aqueous Solution of Ethanol

About 5 kg of peeled onion bulbs cut in 2 to 4 pieces and about 5,000 mL of 34% ethanol were put in a container, and the container was then sealed. The container was then left to stand for 1 to 10 months at room temperature, with occasional stirring. The resulting mixture was separated into solid and liquid and the liquid was concentrated under reduced pressure.

(3) Fraction Extracted from Chinese Chive with an Aqueous Solution of Ethanol

About 5 kg of washed Chinese chive cut into about 5 to 10 cm lengths and about 5,000 mL of 34% ethanol were put in a container, and the container was then sealed. The container was then left to stand for 1 to 10 months at room temperature, with occasional stirring. The resulting mixture was separated into solid and liquid and the liquid was concentrated under reduced pressure.

Production Example 2 Isolation of S-1-propenylcysteine from the Fraction Extracted from Garlic with the Aqueous Solution of Ethanol (1) The fraction extracted from garlic with aqueous solution of ethanol which had been obtained in Production Example 1 (1) was placed in a dialysis tube with a pore size of 3,500 and dialyzed against purified water. Then, external dialysis solution was passed through cation exchange resin Dowex 50W×8(H+), and the resin was thoroughly washed with purified water. The amino acids adsorbed to the resin were eluted with 2 N ammonia and concentrated under reduced pressure. Then, the concentrate thus obtained was loaded on a silica gel column, followed by column chromatography using a chloroform/methanol/water mixture as a solvent. Then, a fraction containing the product of interest (i.e., S-1-propenylcysteine) was collected and concentrated. The concentrate thus obtained was dissolved in water and subjected to chromatography using a preparative reversed-phase column (octadecylsilyl column) and 0.1% formic acid as a solvent. The product of interest was then collected and the solvent was removed by freeze drying. The resulting freeze-dried product was identified as a mixture of trans-S-1-propenylcysteine and cis-S-1-propenylcysteine (trans isomer: cis isomer=8:2) by NMR (solvent: deuterium oxide) and a mass spectrometer based on a comparison with the spectra obtained from standard substances, whose structures are shown below.

trans-S-1-Propenylcysteine $^1$H-NMR (500 MHz, in $D_2O$—NaOD, δ): 1.76 (d, 3H, J=7.0 Hz), 2.98 (dd, 1H, J=7.5, 14.5 Hz), 3.14 (dd, 1H, J=4.5, 14.5 Hz) 3.69 (dd, 1H, J=4.5, 7.5 Hz), 5.10-5.14 (m, 1H), 6.02 (d, 1H, J=15.5 Hz);

$^{13}$C-NMR (125 MHz, in $D_2O$—NaOD, δ): 17.61, 33.53, 53.70, 119.92, 132.12, 172.73.

HRMS: observed $[M+H]^+$=162.0583, calculated $[M+H]^+$=162.0581 cis-S-1-Propenylcysteine $^1$H-NMR (500 MHz, in $D_2O$, δ): 1.74 (d, 3H, J=7.0 Hz), 3.21 (dd, 1H, J=7.5, 15.0 Hz), 3.31 (dd, 1H, J=4.5, 15.0 Hz), 3.95 (dd, 1H, J=4.5, 7.5 Hz), 5.82-5.86 (m, 1H), 6.01 (d, 1H, J=9.5 Hz);

$^{13}$C-NMR (125 MHz, in D$_2$O—NaOD, δ): 13.89, 33.88, 54.16, 122.58, 127.78, 172.63.

HRMS: observed [M+H]$^+$=162.0580, calculated [M+H]$^+$=162.0581

(2) Measurement of S-1-Propenylcysteine in the Fraction Extracted from Garlic with the Aqueous Solution of Ethanol From the fraction extracted from garlic with aqueous solution of ethanol which had been obtained in Production Example 1 (1), 500 mg to 1 g was aliquoted into a container, to which a 20 mM hydrochloric acid solution of S-n-3-butenylcysteine was added as an internal standard. The resulting solution was brought up to 20 mL with 20 mM hydrochloric acid. After thorough stirring, a portion of the solution was centrifuged at 1,750 G for about 10 minutes. Then, a portion of the resulting supernatant was subjected to centrifugal filtration (15,000 rpm, 10 minutes) using a centrifugal filtration unit (Amicon Ultra, cutoff: 3,000). From the filtrate thus obtained, 20 μL was taken and subjected to derivatization using the AccQ·Tag Derivatization Kit (Waters Corporation). Separately, a standard compound was dissolved in 20 mM hydrochloric acid and a standard solution for calibration was prepared by carrying out similar operations to the sample. The sample solution and standard solution were subjected to chromatography using the Acquity UPLC System (Waters Corporation) to determine the content. As a result, S-1-propenylcysteine was 3.7±0.3 mg/g dried product.

Test Examples (1) Sample Preparation

Test solutions for a biological activity evaluation were prepared as follows. In conducting the biological activity evaluation, all the test solutions were prepared at the time of use.
(a) The fractions extracted from the plants belonging to the genus *Allium* with aqueous solutions of ethanol which had been produced in Production Example 1 were dissolved or suspended in purified water so as to achieve a solid content of about 40% (W/V). The resulting solutions were appropriately diluted with purified water for tests. When the solution was used for an in vitro test, it was filtered through a membrane filter and the filtrate was used.
(b) About 1 mg of the S-1-propenylcysteine (a cis/trans mixture) produced in Production Example 2 was accurately weighed out and dissolved in 1 mL of purified water. Using the resulting solution as a stock solution, appropriately diluted solutions were used for tests. When the solution was used for an in vitro test, it was filtered through a membrane filter and the filtrate was used.

(2) Cells for Evaluation Tests

Cells for the biological activity evaluation were prepared as follows. Female C57BL/6N mice for tests were purchased from CLEA Japan, Inc. After the purchase, the mice were acclimated for a week, and then sacrificed and the spleens were taken out. The excised spleens were crushed and passed through a mesh to collect lymphocytes, which were used as the cells for the evaluation test.

(3) Animals for the Evaluation Test

Animals for the biological activity evaluation were reared as follows. Female C57BL/6N mice for tests were purchased from CLEA Japan, Inc. After the purchase, the mice were acclimated for a week, and then used as the animals for the evaluation test.

(4) ELISA

Mouse IgA Quantitation Kit manufactured by Bethyl laboratories, Inc was purchased and the amount of IgA produced was measured. The wash solution or culture supernatant to be measured was placed in a 96-well plate coated with an anti-IgA antibody. After adding various reaction reagents, the absorbance was measured by using a plate reader.

Mouse IL-6 ELISA Ready-SET-Go! Kit manufactured by eBioscience was purchased and the amount of IL-6 produced was measured. The culture supernatant to be measured was placed in a 96-well plate coated with an anti-IL-6 antibody. After adding various reaction reagents, the absorbance was measured by using a plate reader.

(5) Promoting Effect on IgA Production and Inhibitory Effect on IL-6 Production (a-i) Promoting Effect of IgA Production (In Vitro) <1>

The lymphocytes obtained from the cells for the evaluation test of (2) above were prepared at 1×10$^6$ cells/mL with a 10% serum-containing medium and inoculated into a 24-well plate at 1 mL each, or prepared at 1×10$^6$ cells/200 μL and inoculated into a 48-well plate at 200 μL each. Subsequently, of the samples prepared in (1) above, those prepared in (1) (a) above were appropriately diluted and added to the 24-well plate so that the final concentration was 4 mg/mL, and those prepared in (1) (b) was added to the 48-well plate at 0.1 mM. After culturing for three days at 37° C., the supernatants were collected and the amount of IgA was measured by ELISA. The results are shown in FIGS. 1 and 2.

The fractions extracted from the plants belonging to the genus *Allium* with the aqueous solutions of ethanol promoted IgA production more strongly than fresh plant (water was added to each plant in the same weight as the plant, followed by homogenization, and the resulting homogenate was filtered through gauze, and the resulting filtrate was used as the sample) (FIG. 1).

Figure 2:
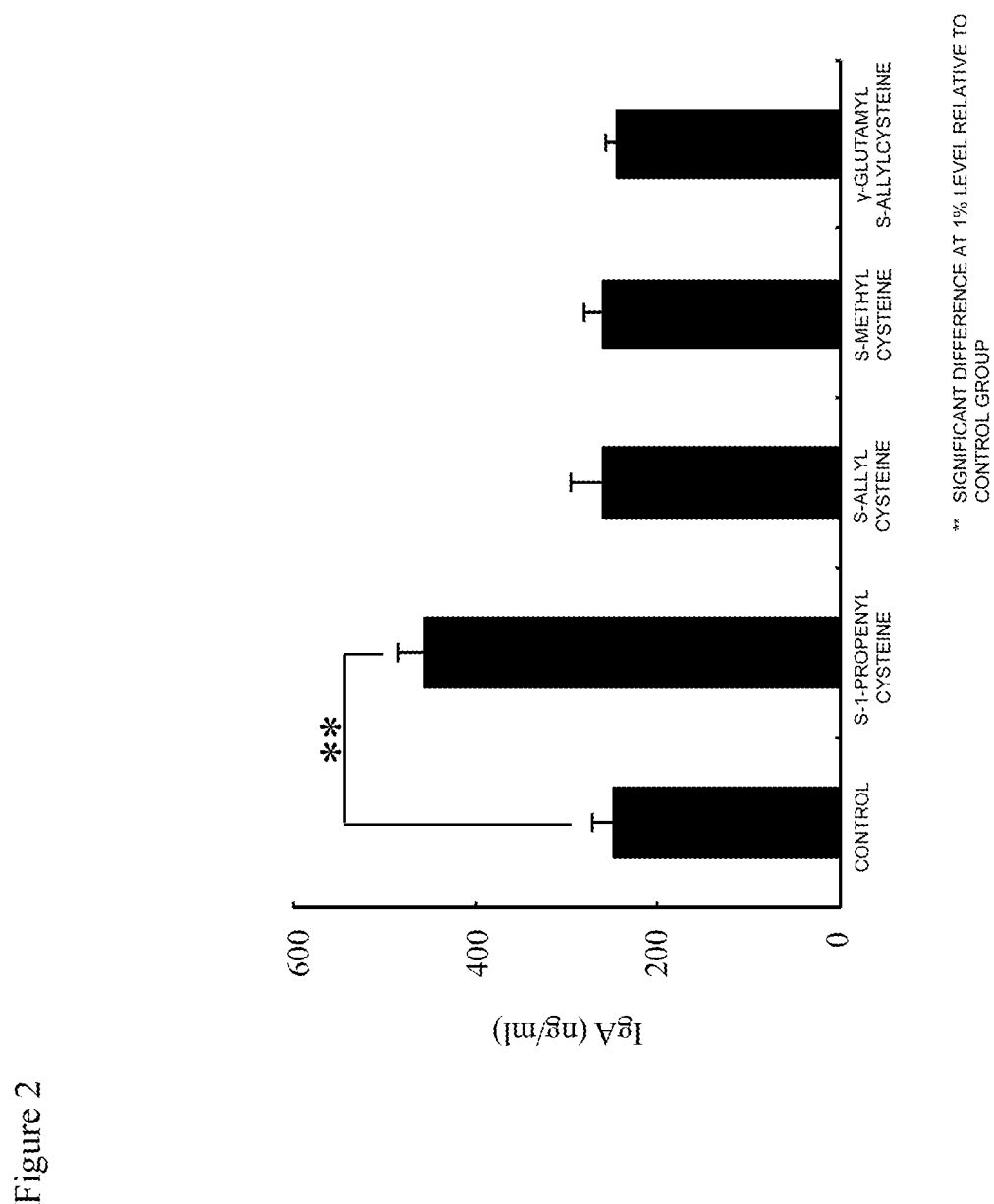
FIG. 2 is a graph illustrating promoting effect of sulfur-containing amino acid compounds on IgA production.

S-1-propenycysteine promoted IgA production more strongly than other sulfur-containing amino acid compounds (FIG. 2).

(a-ii) Promoting Effect of IgA Production (In Vitro) <2>

The lymphocytes obtained from the cells for the evaluation test of (2) above were prepared at 5×10$^6$ cells/mL with a 10% serum-containing medium and inoculated into a 48-well plate at 200 μL each.

To the cells, chemically synthesized cis-S-1-propenycysteine and trans-S-1-propenycysteine, and S-1-propenycysteine (a cis/trans mixture) prepared in Production Example 2 were added at concentrations of 0.03, 0.1, and 0.3 mM, followed by culturing at 37° C. for three days. Subsequently, the amount of IgA produced in the culture supernatants was measured by ELISA. The results are shown in FIG. 8.

The trans isomer and S-1-propenycysteine in which the proportion of trans isomer is higher than that of cis isomer significantly enhanced IgA production. In contrast, cis-S-1-propenycysteine virtually did not affect IgA production.

(b-i) Promoting Effect on IgA Production and Inhibitory Effect on IL-6 Production Under LPS Stimulation (In Vitro) <1>

The lymphocytes obtained from the cells for the evaluation test of (2) above were prepared at 1×10$^6$ cells/mL with a 10% serum-containing medium and inoculated into a 24-well plate at 1 mL each. Subsequently, *Escherichia coli* O55-derived lipopolysaccharides (LPS) were added at 1 μg/mL, and then the samples prepared in (1) (b) above were added at 0.1 mM, followed by culturing at 37° C. for 24 hours or three days. Upon completion of culture, the supernatants were collected and the amounts of IL-6 and IgA were measured by ELISA. The results are shown in FIGS. 6 and 7.

Figure 6:
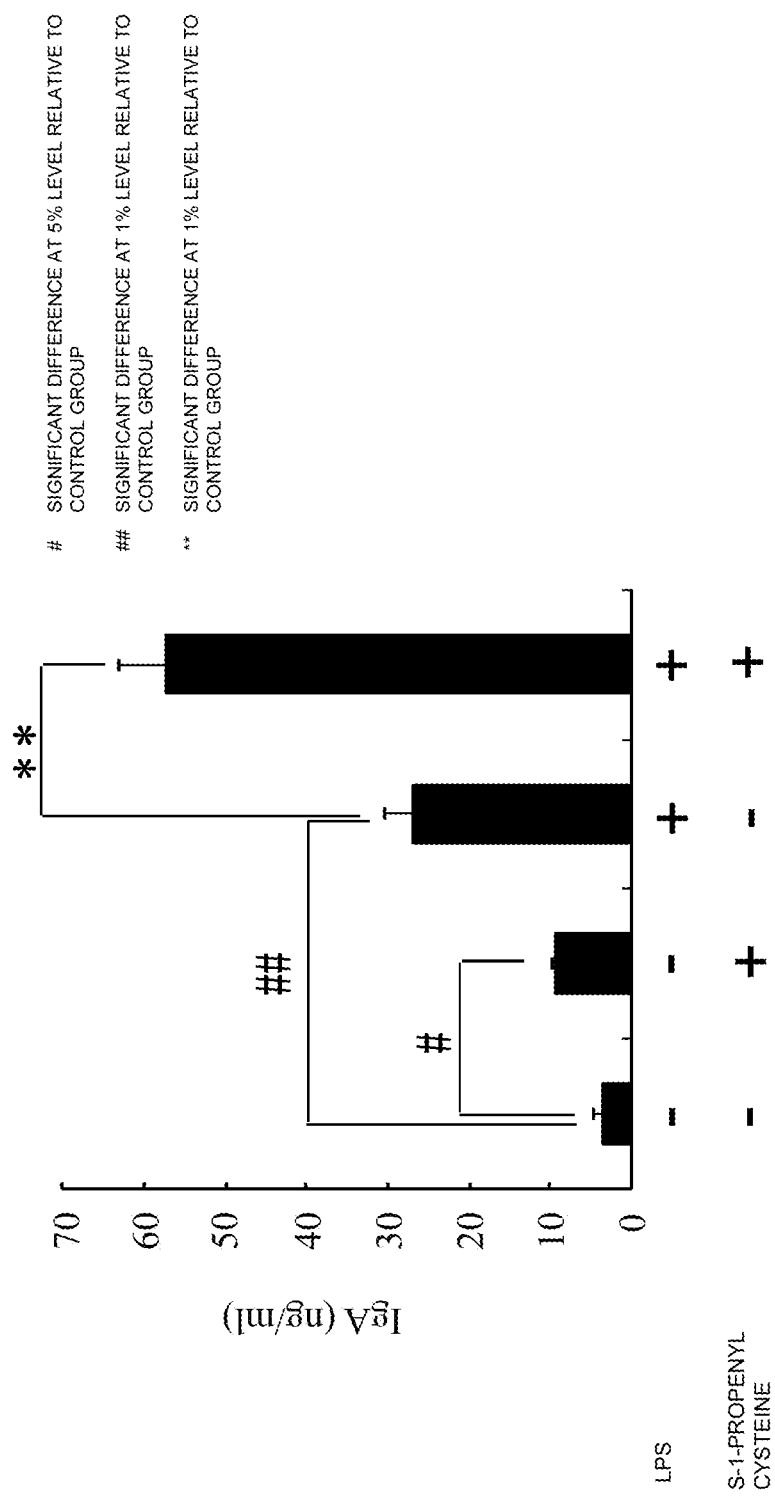
FIG. 6 is a graph illustrating promoting effects of S-1-propenylcysteine on IgA production under LPS stimulation.

Under LPS stimulation, S-1-propenycysteine exhibited higher promoting effect on IgA production than under no stimulation (FIG. 6). The amount of IL-6 secretion induced by LPS stimulation was reduced (FIG. 7).

(b-ii) Inhibitory Effect on IL-6 Production Under LPS Stimulation (In Vitro) <2>

The lymphocytes obtained from the cells for the evaluation test of (2) above were prepared at $5 \times 10^6$ cells/mL with a 10% serum-containing medium and inoculated into a 48-well plate at 200 μL each. To these cells, chemically synthesized cis-S-1-propenycysteine and trans-S-1-propenycysteine, SAC, and S-1-propenycysteine (a cis/trans mixture) prepared in Production Example 2 were added at a concentration of 0.3 mM in the presence of 3 μg/mL Salmonella-derived lipopolysaccharides (LPS), followed by culturing at 37° C. for 24 hours. Upon completion of culture, the supernatants were collected and the amount of IL-6 was measured by ELISA. The results are shown in FIG. 9.

The trans isomer and S-1-propenycysteine in which the proportion of trans isomer is higher than that of cis isomer significantly inhibited IL-6 secretion induced by LPS stimulation (FIG. 9).

(c) Promoting Effect of IgA Production (In Vivo) <1>:

The animals for the evaluation test of (3) above were orally administered with the sample prepared in (1) (b) above for five days, and then sacrificed and the small intestines were removed. Phosphate buffer (5 mL) was passed through the small intestines and the contents of the small intestines and the lavage fluids collected. The collected products were combined and centrifuged, and the amount of IgA in the resulting supernatant was quantified by ELISA. The results are shown in FIG. 3.

Figure 3:
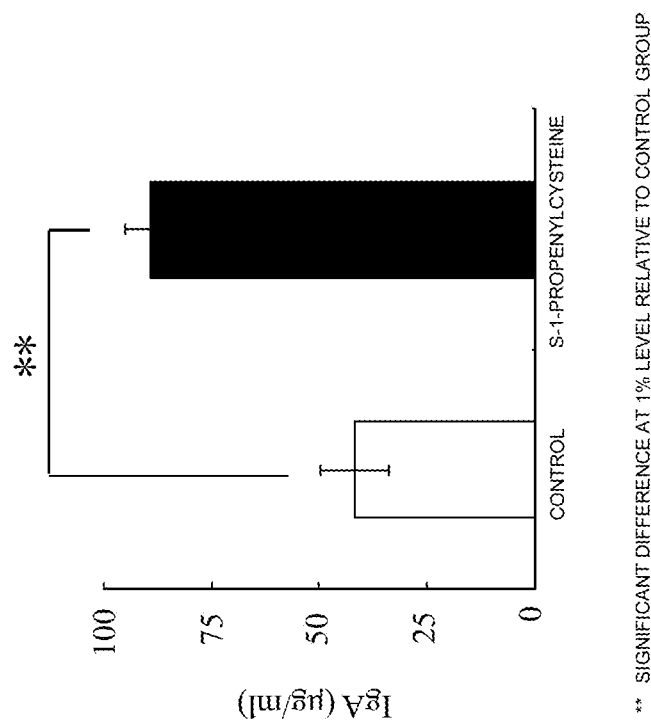
FIG. 3 is a graph illustrating promoting effects of S-1-propenycysteine on the amount of IgA production.

In the S-1-propenycysteine administration group, the amount of IgA in the intestinal lavage fluids was increased, as compared to that in the water administration group (FIG. 3).

(d) Promoting Effect of IgA Production (In Vivo) <2>:

The animals for the evaluation test of (3) above were orally administered with the sample prepared in (1) (b) above for five days, and then sacrificed. The small intestines were removed, from which Peyer's patches were collected. The Peyer's patches were ground, to which Collagenase D was added to give a final concentration of 1 mg/mL and DNAase I was added to give a final concentration of 20 μg/mL. Treatment was continued for 30 minutes while shaking at 37° C., followed by centrifugation at 1,500 rpm. The resulting supernatant was removed. Then, 2 mL of 5% FBS-containing Hank's Balanced Salt Solution containing 5 mM EDTA was added, followed by treatment for five minutes while shaking at 37° C. Upon completion of treatment, the resultant was passed through a 40 μm mesh to remove tissue pieces and collect lymphocytes. To block Fc receptors (FcR), the lymphocytes thus collected was added with 20 μL of an FcR blocking reagent diluted 10-fold with 2% FBS-containing phosphate buffer, followed by treatment for 30 minutes at 4° C. Then, 20 μL of a phycoerythrin (PE)-labeled anti-mouse CD45 antibody (B220) and 20 μL of a fluorescein isothiocyanate (FITC)-labeled anti-mouse immunoglobulin A antibody were added, followed by treatment for 30 minutes at 4° C. Upon completion of treatment, $1 \times 10^4$ lymphocytes were analyzed by using a flow cytometer to count the number of IgA-producing B cells which reacted to the anti-mouse CD45 antibody (B220) and the anti-mouse immunoglobulin A antibody. The results are shown in FIG. 4.

Figure 4:
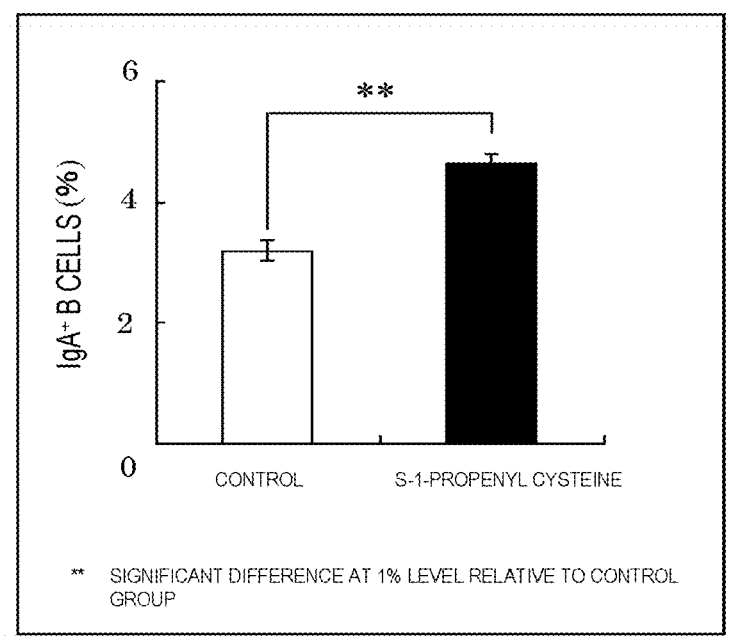
FIG. 4 is a graph illustrating promoting effects of S-1-propenylcysteine on the number of IgA-producing cells in Peyer's patches.

In the S-1-propenycysteine administration group, the number of IgA-producing B cells was increased, as compared to that in the water administration group (FIG. 4).

(e) Promoting Effect of IgA Production (In Vivo) <3>:

The animals for the evaluation test of (3) above were orally administered with the sample prepared in (1) (b) above for five days. The animals were sacrificed and a laparotomy was performed without breaking the peritoneum. Then, 3 mL of 5% FBS-containing Hank's Balanced Salt Solution was placed in a 5 mL syringe and injected into the peritoneal cavity using a 27G needle. Then, the peritoneum was pressed with fingers to spread the injected solution evenly throughout the peritoneal cavity, followed by collecting the intraperitoneal solution using a 18G needle. The intraperitoneal solution thus collected was centrifuged at 1,500 rpm for five minutes. The resulting supernatant was removed and peritoneal cells were collected. To the peritoneal cells thus collected, 20 μL of an FcR blocking reagent diluted 10-fold with 2% FBS-containing phosphate buffer was added to block FcR, followed by treatment for 30 minutes at 4° C. Then, 20 μL of a PE-labeled anti-mouse CD45 antibody (B220) and 20 μL of a FITC-labeled anti-mouse immunoglobulin A antibody were added, followed by treatment for 30 minutes at 4° C. Upon completion of treatment, $1 \times 10^4$ lymphocytes were analyzed by using a flow cytometer to count the number of IgA-producing B cells which reacted to the anti-mouse CD45 antibody (B220) and the anti-mouse immunoglobulin A antibody. The results are shown in FIG. 5.

Figure 5:
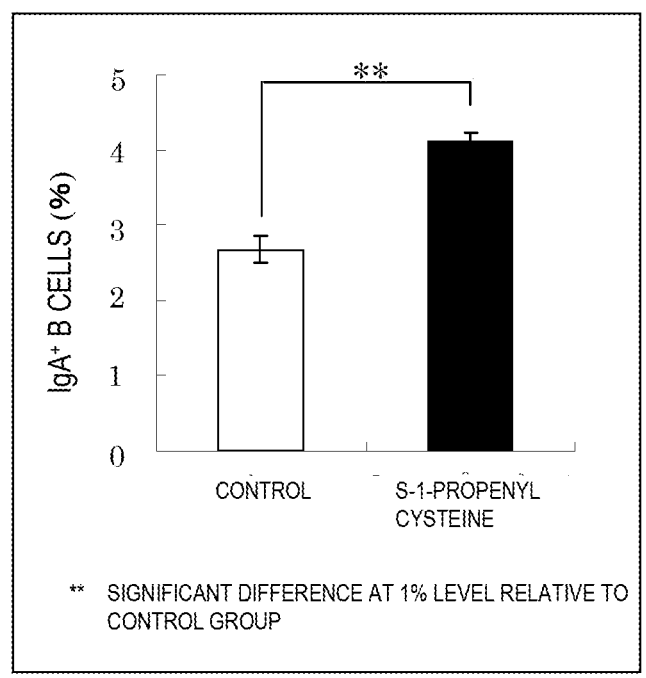
FIG. 5 is a graph illustrating promoting effects of S-1-propenycysteine on the number of IgA-producing cells in the peritoneal cavity.

In the S-1-propenycysteine administration group, the number of IgA-producing B cells was increased, as compared to that in the water administration group (FIG. 5).

The invention claimed is:

1. A method for immunomodulation, comprising administering S-1-propenylcysteine or a salt thereof to a subject in need thereof.

2. The method of claim 1, wherein the S-1-propenylcysteine or a salt thereof has a proportion of trans isomer of from 50 to 100%, where the sum total of trans and cis isomers is 100%.

3. The method of claim 1, wherein the S-1-propenylcysteine or a salt thereof promotes IgA production and/or inhibits IL-6 production.

4. The method according to claim 1, wherein the S-1-propenylcysteine or a salt thereof is derived from one or more plants belonging to the genus Allium selected from the group consisting of garlic, onion, elephant garlic, Chinese chive, and Welsh onion.

5. The method according to claim 4, wherein the S-1-propenylcysteine or a salt thereof is obtained by extracting the plant belonging to the genus Allium in a 10 to 50% aqueous solution of ethanol at 0 to 80° C. for one month or more, allowing the extract thus obtained to adsorb to a cation exchange resin, carrying out elution using 0.1 to 3 N ammonia water, and then subjecting the eluate thus obtained to silica gel column chromatography and/or reversed-phase column chromatography to collect S-1-propenylcysteine or a salt thereof.

6. The method according to claim 1, wherein the S-1-propenylcysteine or a salt thereof is in a form of a medicine.

7. The method according to claim 1, wherein the S-1-propenylcysteine or a salt thereof is in a form of a food.

* * * * *